(12) United States Patent
Whitman

(10) Patent No.: US 6,695,199 B2
(45) Date of Patent: *Feb. 24, 2004

(54) FLUID DELIVERY MECHANISM FOR USE WITH ANASTOMOSING, STAPLING, AND RESECTING INSTRUMENTS

(75) Inventor: Michael P. Whitman, New Hope, PA (US)

(73) Assignee: Power Medical Interventions, Inc., New Hope, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/314,731

(22) Filed: Dec. 9, 2002

(65) Prior Publication Data
US 2003/0089757 A1 May 15, 2003

Related U.S. Application Data

(63) Continuation of application No. 09/510,932, filed on Feb. 22, 2000, now Pat. No. 6,491,201.

(51) Int. Cl.$^7$ ............................................. A61B 17/04
(52) U.S. Cl. ...................................... 227/180.1; 604/43
(58) Field of Search ..................... 227/19, 155, 176.1, 227/179.1, 180.1; 604/43, 544

(56) References Cited

U.S. PATENT DOCUMENTS

| | | | |
|---|---|---|---|
| 1,881,250 A | 10/1932 | Tomlinson | |
| 3,079,606 A | 3/1963 | Bobrov et al. | |
| 3,490,675 A | 1/1970 | Green et al. | |
| 3,494,533 A | 2/1970 | Green et al. | |
| 3,618,842 A | 11/1971 | Bryan | |
| 3,662,939 A | 5/1972 | Bryan | |
| 3,815,476 A | 6/1974 | Green et al. | |
| 4,071,029 A | 1/1978 | Richmond et al. | |
| 4,207,898 A | 6/1980 | Becht | |

(List continued on next page.)

FOREIGN PATENT DOCUMENTS

| | | |
|---|---|---|
| EP | 0 116 220 | 8/1984 |
| EP | 0 121 474 | 10/1984 |
| EP | 0 156 774 | 10/1985 |
| EP | 0 216 532 | 4/1987 |
| EP | 0 399 701 | 11/1990 |
| EP | 0 514 139 | 11/1992 |
| EP | 0 536 903 | 4/1993 |
| EP | 0 539 762 | 5/1993 |
| EP | 0 552 050 | 7/1993 |
| EP | 0 593 920 | 4/1994 |
| EP | 0 621 006 | 10/1994 |
| FR | 2660851 | 10/1991 |
| GB | 2 044 108 | 10/1980 |
| GB | 2180455 | 4/1987 |
| WO | WO 82/03545 | 10/1982 |
| WO | WO 83/00992 | 3/1983 |
| WO | WO 90/05491 | 5/1990 |
| WO | WO 91/07136 | 5/1991 |
| WO | WO 92/16141 | 10/1992 |
| WO | WO 93/08754 | 5/1993 |
| WO | WO 95/35065 | 12/1995 |
| WO | WO 99/20328 | 4/1999 |

*Primary Examiner*—Edward K. Look
*Assistant Examiner*—John K Fristoe, Jr.
(74) *Attorney, Agent, or Firm*—Kenyon & Kenyon

(57) ABSTRACT

A medicine delivery mechanism or fibrin injection mechanism for use in combination with an anastomosing and stapling attachment for an electromechanical device driver comprises a dispensing chamber with an elongated cylindrical cross section (although other shapes can be used) which is formed in the staple housing of the attachment in lieu of a staple port or staple ports, and which has a mouth forming a channel lined at its innermost edge perimeter with inward facing prongs or teeth. The dispensing chamber contains a sac filled with fibrin. A delivery or plunger driver travels within the dispensing chamber to press a sac of fibrin against the inward facing prongs, tearing the sac and releasing the fibrin to push the fibrin through the channel to the treatment site.

38 Claims, 5 Drawing Sheets

U.S. PATENT DOCUMENTS

| | | | |
|---|---|---|---|
| 4,286,585 A | 9/1981 | Ogawa | |
| 4,289,133 A | 9/1981 | Rothfuss | |
| 4,429,695 A | 2/1984 | Green | |
| 4,442,964 A | 4/1984 | Becht | |
| 4,445,509 A | 5/1984 | Auth | |
| 4,484,503 A | 11/1984 | Sitte et al. | |
| 4,520,817 A | 6/1985 | Green | |
| 4,535,773 A | 8/1985 | Yoon | |
| 4,589,582 A | 5/1986 | Bilotti | |
| 4,605,001 A | 8/1986 | Rothfuss et al. | |
| 4,606,343 A | 8/1986 | Conta et al. | |
| 4,610,383 A | 9/1986 | Rothfuss et al. | |
| D286,567 S | 11/1986 | Lichtman et al. | |
| 4,631,052 A | 12/1986 | Kensey | |
| 4,655,673 A | 4/1987 | Hawkes | |
| 4,671,445 A | 6/1987 | Barker et al. | |
| 4,705,038 A | 11/1987 | Sjostrom et al. | |
| 4,742,815 A | 5/1988 | Ninan et al. | |
| 4,756,309 A | 7/1988 | Sachse et al. | |
| 4,771,774 A | 9/1988 | Simpson et al. | |
| 4,781,186 A | 11/1988 | Simpson et al. | |
| 4,784,131 A | 11/1988 | Kulik et al. | |
| 4,813,928 A | 3/1989 | Abe et al. | |
| 4,867,158 A | 9/1989 | Sugg | |
| 4,887,599 A | 12/1989 | Muller | |
| 4,890,602 A | 1/1990 | Hake | |
| 4,892,244 A | 1/1990 | Fox et al. | |
| 4,893,613 A | 1/1990 | Hake | |
| 4,928,699 A | 5/1990 | Sasai | |
| 4,936,845 A | 6/1990 | Stevens | |
| 4,955,882 A | 9/1990 | Hakky | |
| 4,976,688 A | 12/1990 | Rosenblum | |
| 4,982,726 A | 1/1991 | Taira | |
| 4,995,877 A | 2/1991 | Ams et al. | |
| 5,005,749 A | 4/1991 | Aranyi | |
| 5,040,715 A | 8/1991 | Green et al. | |
| 5,059,203 A | 10/1991 | Husted | |
| 5,071,430 A | 12/1991 | de Salis et al. | |
| 5,077,506 A | 12/1991 | Krause | |
| 5,104,025 A | 4/1992 | Main et al. | |
| 5,133,359 A | 7/1992 | Kedem | |
| 5,133,729 A | 7/1992 | Sjostrom | |
| 5,139,513 A | 8/1992 | Segato | |
| 5,170,925 A | 12/1992 | Madden et al. | |
| 5,171,247 A | 12/1992 | Hughett et al. | |
| 5,171,251 A | 12/1992 | Bregen et al. | |
| 5,192,292 A | 3/1993 | Cezana et al. | |
| 5,197,649 A | 3/1993 | Bessler et al. | |
| 5,205,459 A | 4/1993 | Brinkerhoff et al. | |
| 5,207,691 A | 5/1993 | Nardella | |
| 5,221,279 A | 6/1993 | Cook et al. | |
| 5,224,951 A | 7/1993 | Freitas | |
| 5,226,426 A | 7/1993 | Yoon | |
| 5,237,884 A | 8/1993 | Seto | |
| 5,249,583 A | 10/1993 | Mallaby | |
| 5,258,007 A | 11/1993 | Spetzler et al. | |
| 5,258,008 A | 11/1993 | Wilk | |
| 5,261,877 A | 11/1993 | Fine et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,279,565 A | 1/1994 | Klein et al. | |
| 5,285,945 A | 2/1994 | Brinkerhoff et al. | |
| 5,289,963 A | 3/1994 | McGarry et al. | |
| 5,290,299 A | 3/1994 | Fain et al. | |
| 5,292,053 A | 3/1994 | Bilotti et al. | |
| 5,312,023 A | 5/1994 | Green et al. | |
| 5,318,221 A | 6/1994 | Green et al. | |
| 5,326,013 A | 7/1994 | Green et al. | |
| 5,330,486 A | 7/1994 | Wilk | |
| 5,333,773 A | 8/1994 | Main et al. | |
| 5,342,382 A | 8/1994 | Brinkerhoff et al. | |
| 5,344,420 A | 9/1994 | Hilal et al. | |
| 5,350,104 A | 9/1994 | Main et al. | |
| 5,368,607 A | 11/1994 | Freitas | |
| 5,380,321 A | 1/1995 | Yoon | |
| 5,383,880 A | 1/1995 | Hooven | |
| 5,395,030 A | 3/1995 | Kuramoto et al. | |
| 5,395,033 A | 3/1995 | Byrne et al. | |
| D357,535 S | 4/1995 | Grant et al. | |
| 5,403,326 A | 4/1995 | Harrison et al. | |
| 5,403,327 A | 4/1995 | Thornton et al. | |
| 5,411,508 A | 5/1995 | Bessler et al. | |
| 5,413,267 A | 5/1995 | Solyntjes et al. | |
| 5,425,738 A | 6/1995 | Gustafson et al. | |
| 5,433,721 A | 7/1995 | Hooven et al. | |
| 5,441,507 A | 8/1995 | Wilk | |
| 5,467,911 A | 11/1995 | Tsuruta et al. | |
| 5,482,197 A | 1/1996 | Green et al. | |
| 5,485,947 A | 1/1996 | Olson et al. | |
| 5,518,163 A | 5/1996 | Hooven | |
| 5,518,164 A | 5/1996 | Hooven | |
| 5,533,661 A | 7/1996 | Main et al. | |
| 5,549,565 A | 8/1996 | Ryan et al. | |
| 5,588,579 A | 12/1996 | Schnut et al. | |
| 5,599,347 A | 2/1997 | Hart et al. | |
| 5,639,008 A | 6/1997 | Gallagher et al. | |
| 5,653,374 A | 8/1997 | Young et al. | |
| 5,662,673 A | 9/1997 | Kieturakis | |
| 5,667,517 A | 9/1997 | Hooven | |
| 5,693,031 A | 12/1997 | Ryan et al. | |
| 5,709,335 A | 1/1998 | Heck | |
| 5,732,872 A | 3/1998 | Bolduc et al. | |
| 5,749,893 A | 5/1998 | Vidal et al. | |
| 5,758,814 A | 6/1998 | Gallagher et al. | |
| 5,779,130 A | 7/1998 | Alesi et al. | |
| 5,782,396 A | 7/1998 | Mastri et al. | |
| 5,817,113 A | 10/1998 | Gifford, III et al. | |
| 5,868,760 A | 2/1999 | McGuckin, Jr. | |
| 5,871,471 A | 2/1999 | Ryan et al. | |
| 5,881,943 A | 3/1999 | Heck et al. | |
| 5,947,363 A | 9/1999 | Bolduc et al. | |
| 5,954,259 A | 9/1999 | Viola et al. | |
| 5,957,882 A | 9/1999 | Nita et al. | |
| 5,984,919 A | 11/1999 | Hilal et al. | |
| 5,997,510 A | 12/1999 | Schwemberger | |
| 6,119,913 A | 9/2000 | Adams et al. | |
| 6,126,058 A | 10/2000 | Adams et al. | |

A-A'

FLUID DELIVERY MECHANISM FOR USE WITH ANASTOMOSING, STAPLING, AND RESECTING INSTRUMENTS

CROSS-REFERENCE TO RELATED APPLICATIONS

This application is a continuation of U.S. patent application Ser. No. 09/510,932, which was filed on Feb. 22, 2000, now U.S. Pat. No. 6,491,201, each of which is expressly incorporated herein in its entirety by reference thereto.

BACKGROUND OF THE INVENTION

1. Field of the Invention

The present invention relates generally to a fluid delivery mechanism for use with anastomosing, stapling, and resecting surgical tools, and more specifically to a fibrin injection mechanism by which such tools may deliver fibrin to the stapling and cutting site of a resected colon.

2. Description of the Prior Art

Upon identification of cancerous or other anomalous tissue in the gastrointestinal tract, surgical intervention is often prescribed. The field of cancer surgery, and more specifically, the surgical procedure by which a section of the gastrointestinal tract which includes cancerous or anomalous tissue is resected, includes a number of uniquely designed instruments. In combination with a description of the present instrumentation and their functions, a description of the state of the art in this surgical procedure shall also be provided.

The first question which must be answered when determining how to treat gastrointestinal cancer relates to the specific location of the cancerous tissue. This is very important insofar as the instruments which are provided in the present art have limitations relating to how far they may be inserted into the gastrointestinal tract. If the cancerous tissue is too far up the colon, for example, then the standard instrumentation provided is unusable, thus requiring special accommodations. These accommodations generally increase the risk of contamination of the surrounding tissues with bowel contents, increase the length of the surgery and the corresponding need for anesthesia, and eliminate the benefits of precise anastomosing and stapling which comes from utilizing a mechanized device.

More specifically, in the event that the cancerous tissue is located at a position in the colon which is accessible by the present instrumentation, the patient's abdomen is initially opened to expose the bowel. The surgeon then utilizes a linear cutter and stapling device which cuts the tube of the colon on either side of the cancerous tissue, thereby creating two stapled ends of the bowel (a distal end which is directed toward the anus, and the proximal end which is closest to the small intestine). This is done in order to temporarily minimize contamination.

More particularly, referring to FIG. 1, the bowel is placed between the scissoring elements 1, 2 at the tip of the linear stapling instrument 5. By squeezing the trigger 3 in the handle 4 of the device, the surgeon causes the scissoring elements 1, 2 to come together. A second trigger (or a secondary action of the same trigger) is then actuated to drive a series of staples 6 through the clamped end of the colon, thereby closing and transecting the ends.

The surgeon then partially opens the proximal end and inserts the removable anvil portion of an anastomosing and stapling instrument into the exposed proximal end. This step, as well as those of the remainder of the surgical procedure, are related to the functioning of this surgical instrument. More particularly, and with respect to FIG. 2, the surgeon begins by taking the instrument 7 and manually turning the dial 8 at the base of the handle 9 which causes the anvil head 10 at the opposite end to advance forward. The surgeon continues to turn the dial 8 until the anvil head 10 advances to its most extreme extended position. This manual turning requires nearly thirty full rotations. Once fully extended, the anvil head of the instrument is decoupled therefrom and is inserted into the partial opening of the proximal end such that the coupling post extends outwardly therethrough. This partial opening of the proximal end is then sutured closed. The extending shaft 11 of the anastomosing and stapling instrument 7 is then inserted and advanced into the lower colon, transanally, until the coupling stem 12 thereof extends through the stapled distal end. The surgeon then joins the coupling ends of the anvil and shaft together and begins to manually rotate the dial in the handle again, this time bringing the anvil head closer to the end 13 of the shaft.

Once the anvil head and shaft are brought close together, after the surgeon has manually rotated the dial another thirty times, a grip-style trigger 14 in the handle is manually actuated. This actuation causes a circular blade 15 to advance axially out from the tip of the shaft, and into contact with the opposing face 16 of the anvil 10. The blade cuts through the stapled-closed ends of the proximal and distal ends of the colon, thereby also cutting a new pair of ends of the proximal and distal portions of the colon. The tissue which has been severed is held in an interior volume at the end of the shaft.

In lock step with the cutting, the freshly opened ends are joined together by a series of staples 17 which are advanced through holes in the perimeter of the tip of the shaft (being pressed against and closed by the opposing face of the anvil). The coupled shaft and anvil are then withdrawn from the patient.

As with many such devices of the prior art, all of the above devices are considered fully disposable, and are, in fact, thrown away after a single use. They are complicated devices, having multiple moving parts, requiring substantial structural integrity and, therefore, expense in manufacturing. The fact that they are used only once, and no part can be used again render the use of such devices expensive and wasteful of resources.

In addition to this failure, as can be readily observed from the preceding descriptions, the prior art devices suffer from numerous other limitations which would be desirable to overcome. These include the requirement that the surgeon manually actuate a number of different functions (including those associated with the dial and trigger of the anastomosing and stapling instrument and the multiple triggers of the cutting and stapling instrument).

Another failure is that the prior art devices provide no means to allow the delivery of fluid to the site of the freshly cut tissue. Medicine or other substances which accelerate the healing process, if delivered to the site simultaneous with or subsequent to the stapling and cutting process, could speed healing of the tissue or perform other medical functions. One such substance is fibrin, which is the principal protein component of connective tissue, and serves as the fundamental element of the tissue-mending process, specifically the process of scar formation at the joining of two previously separate tissues. Therefore, the ability to inject such a substances at the site of the freshly stapled and cut tissue would provide an advantage over the prior art devices, which make no provision for such delivery.

Therefore, it is a principal object of the present invention to provide a medicine delivery mechanism which can effect such medicine delivery at the stapling and cutting site of targeted tissue.

It is also a principal object of the present invention to provide such a medicine delivery mechanism in a form integral with an instrument for cutting, anastomosing, and stapling, which reduces the waste of resources by permitting the reuse of portions thereof.

It is further an object of the present invention to provide such a medicine delivery mechanism which reduces the requirements for the surgeon to manually actuate different components and mechanisms.

Other objects of the present invention shall be recognized in accordance with the description thereof provided hereinbelow, and in the Detailed Description of Preferred Embodiments in conjunction with the remaining Figures.

SUMMARY OF THE INVENTION

The preceding objects of the invention are provided by a medicine delivery mechanism which is integral with an anastomosing and stapling attachment which has been coupled to an electromechanical driver assembly.

Such an electromechanical driver assembly is shown in FIG. 3 and has a handle 150 and a flexible drive shaft 155. The handle 150 has a pistol grip-styled design, having one or more, and preferably two, finger triggers 160 which are independently coupled to at least one, and preferably two separate motors 165 which each turn separate flexible drive shafts 170 (described more fully, hereinbelow). The motors 165 are each dual direction motors, and are coupled to a manual drive switch 172 to the top of the handle, by which the user can selectively alter the turning direction of each motor. This dual direction capacity may be most simply achieved by selecting motors which turn in a direction corresponding to the direction of current, and actuation of the drive switches alters the direction of the current accordingly. In this example, the power source 175 supplying the motors must be a direct current source, such as a battery pack (and most desirably, a rechargeable battery pack). In the event that the device should be useable with an alternating current, either a transformer can be included, or a more sophisticated intermediate gearing assembly may be provided. In conjunction with the present description, the embodiments of the present invention which will be described utilize a rechargeable battery pack providing a direct current.

In addition to the motor components, the handle further includes several other features, including a remote status indicator 180, a shaft steering means 185, and an on/off switch (not shown). First, the remote status indicator may comprise an LCD (or similar read out device) by which the user may gain knowledge of the position of components (for example whether a clamping element is in the proper position prior to the driving of the staples). Second, the handle also includes a manually actuateable steering means, for example, a joystick or track ball, for directing the movement of the flexible shaft (by means of guidewires implanted in the shaft portion described more fully hereinbelow). Finally, the handle may include an additional electrical power supply and an on/off switch for selectively supplying electrical power to the attachments.

More particularly, with respect to the flexible shaft, the shaft comprises a tubular sheath 195, preferably formed of a simple elastomeric material which is tissue compatible and which is sterilizable (i.e., is sufficiently rugged to withstand an autoclave). Various lengths of this shaft may be provided. The flexible shaft and the handle portions can be separable. If separable, the interface between the proximal end of the shaft and the distal end of the handle should include a coupling means for the drive components.

Specifically regarding the drive components of the shaft, within the elastomeric sheath are a pair of smaller fixed tubes 215 which each contain a flexible drive shaft 220 which is capable of rotating within the tube. The flexible drive shaft, itself, translates a torque from the motor in the handle to the distal end of the shaft, but is flexible enough to be bent, angled, curved, etc. as the surgeon deems necessary to "snake" through the colon of the patient. In order for the distal end of the drive shaft to couple with an attachment, such as the anastomosing and stapling attachment discussed herein, however, the distal tips of the drive shafts must have a conformation which permits the continued translation of torque. For example, the distal tips 200 of the drive shafts may be hexagonal, thereby fitting into a hexagonal recess in the coupling interface of the attachment. Appropriate gearing mechanisms may be provided at the distal end of the shaft, or in the interfacing portion of the attachment, to ensure that the appropriate torque is provided to the attachment.

As suggested above, in conjunction with the manually actuateable steering means mounted to the handle, the sheath further includes at least two guidewires 205 which are flexible, but are coupled to the inner surface of the sheath near the distal end thereof. The guidewires may be axially translated relative to one another by actuation of the steering means, which action causes the sheath to bend and curve accordingly.

Also as suggested above, in conjunction with the LCD indicator of the handle, the shaft further contains an electrical lead 210 for coupling to the attachments. This electrical lead channels a signal from the attachment to the handle for indicating the status of the attachment (for example, whether the anvil portion is in close proximity to the SBR portion, so that the surgeon knows it is safe to staple). Similarly, a second electrical lead may be provided to supply power to separate aspects of the attachment if so required.

As stated above, the present invention is designed to be integral with an anastomosing and stapling attachment for the electromechanical device driver. Such an anastomosing and stapling attachment comprises an anvil portion, and a staple, blade and reservoir portion (SBR portion), which includes a pair of turning drive shafts which are coupleable to the drive components of the shaft element described above, and a corresponding pair of advancing and retracting nuts mounted to the turning drive shafts, but which are prevented from rotating and therefore linearly advance and retract along the shafts when they turn.

The anvil portion is bullet shaped, having a blunt nosed top portion, a flat cutting support surface on the bottom, and a freely rotating coupling post extending axially from the bottom surface. This coupling post is designed to be selectively coupleable and removable from the corresponding nut mounted to one of the turning drive shafts.

The SBR portion is cylindrical in shape, forming a housing which has a hollow interior. It is this hollow interior which forms the reservoir. On the axially outward facing surface of the cylindrical wall of the housing are a series of staple ports, through which the staples of the device are discharged. A series of staple drivers are mounted within the cylindrical walls, beneath the staple ports, for driving the staples therethrough. More accurately, the staple drivers are a series of protuberances on the outer edge of a single cylindrical component which seats in the wall of the SBR portion. The staples, prior to being discharged, are mounted in the holes; and they are advanced through the holes by the forward motion of the staple driver and the protuberances thereof.

The blade is similarly cylindrical, and seats in the inside of the housing, against the inner surface of the wall thereof. Both the blade and the staple driver are mounted to the second nut, which is, in turn, mounted to the other turning drive shaft. As the tuning drive shaft rotates, the nut (which is constrained against rotating) advances along the shaft, thus linearly advancing the blade and staple driver. The blade and the staple driver are, therefore, selectively advanceable axially outward from the housing, in accordance with actuation of the appropriate trigger on the handle.

In order to accelerate the healing process, the attachment is fitted with the present invention, i.e., a mechanism for delivering medicine or a healing substance such as fibrin at the cutting and stapling site, immediately after the cutting and stapling action described above. This mechanism can take on any of several embodiments, two of which are described hereinbelow as examples. In general terms, the present invention comprises a dispensing chamber containing a fluid, a channel communicating between a treatment site and the dispensing chamber, and a delivery or plunger driver traveling within the dispensing chamber with a force greater than the force needed to push the fluid through the channel.

In the preferred embodiment, the present invention comprises a dispensing chamber with an elongated cylindrical cross section (although other shapes can be used) which is formed in the staple housing of the attachment in lieu of a staple port or staple ports. That is, the staple housing contains staple ports as well as a plurality of such dispensing chambers, with all such dispensing chambers having identical parts and identical functions as described herein. The mouth of the dispensing chamber forms a channel lined at its innermost edge perimeter with inward facing prongs or teeth. The dispensing chamber contains a sac filled with fibrin. A delivery or plunger driver travels within the dispensing chamber. The delivery or plunger driver protrudes from the innermost end of the dispensing chamber, similar to the way each staple protrudes from its staple port in the staple housing.

When the turning drive shaft of the attachment (which is connected to the electromechanical driver to drive the staple driver(s) and blade driver) is activated (via the trigger on the electromechanical driver handle), the staple driver moves forward to push a plurality of staples through corresponding staple ports in the staple housing and against the anvil of the attachment to pass through and staple together the target tissue. At the same time, the staple driver moves forward to push each delivery or plunger driver through its corresponding dispensing chamber. As each delivery or plunger driver moves forward through the dispensing chambers, it presses the sac of fibrin against the prongs. As the sac presses against the inward facing prongs of the channel, it tears, releasing the fibrin out through the channel and onto the newly stapled tissue. Meanwhile, the blade driver has moved forward, pushing the blade through the newly stapled tissue and cutting away the excess. The attachment is removed, and the healing process begins, accelerated by the presence of the fibrin at the cutting and stapling site.

In an alternate embodiment, the channel does not have inward facing prongs. Instead, the channel is clear. However, in lieu of a sac of fibrin and a separate delivery or plunger driver, the dispensing chamber is loaded with a cannula having a sharp point. The sharp end of the cannula is pointed toward the stapling surface (that is, when pushed out the dispensing chamber, it will puncture the tissue and eventually be stopped by the flat cutting surface of the anvil). Immediately inside the sharp end of the cannula, the inner perimeter of the cannula is lined with inward facing prongs, similar to the inward facing prongs of the preferred embodiment. Inside the cannula sits a sac of fibrin. Behind the sac of fibrin is located a delivery or plunger driver. This delivery or plunger driver is attached to the walls of the cannula, but is set to break away from the walls after the tip of the cannula has reached the anvil. That is, when the turning drive shaft of the attachment is activated, the staple driver moves forward to push a plurality of staples through corresponding staple ports in the staple housing and against the anvil of the attachment to pass through and staple together the target tissue. At the same time, the staple driver moves forward to push each delivery or plunger driver. The delivery or plunger driver first pushes the cannula out the dispensing chamber and through the tissue, against the anvil. Once the tip of the cannula has reached the anvil, the delivery or plunger driver continues to be pushed forward. This motion breaks the delivery or plunger driver away from the walls of the cannula, and thereafter the driver can continue to move forward through the cannula itself. As each delivery or plunger driver moves forward through its cannula, it presses the sac of fibrin against the prongs. As the sac presses against the inward facing prongs of the cannula, it tears, releasing the fibrin out through the cannula and onto the opposingside of the newly stapled tissue. Meanwhile, the blade driver has moved forward, pushing the blade through the newly stapled tissue and cutting away the excess. The attachment is removed, and the healing process begins, accelerated by the presence of the fibrin at the cutting and stapling site.

Still another embodiment can involve a compressible connection between the delivery driver and the cannula, instead of a break-away portion as described immediately above. For example, springs can be used to connect the delivery driver to the cannula. This would maintain rigidity of the cannula-driver assembly during the initial travel of the cannula to the anvil, as well as permit the delivery driver to continue its forward motion to press against the sac. That is, once the cannula tip has reached the anvil and stopped, the delivery driver will continue to be pushed forward as the springs compress, allowing the delivery driver to press against the sac. The remainder of the operation of the device would be as described above. A unique aspect of this embodiment is that the assembly could be re-used. Instead of the connection between the delivery driver and the cannula being destroyed, the springs would return to their original state after operation of the device, and the assembly could be sterilized and prepared for another application.

It should be noted that various embodiments can be used in conjunction with one another, so as to reach both sides of the treatment site during the same procedure. For example, the embodiment not involving the cannula can reach the proximal side of the treatment site, whereas the embodiment involving the cannula can reach the distal side of the treatment site.

In practice, this attachment is utilized once the section of the colon which is to be removed has been resected (but prior to the linear clamping and stapling step is complete), in the following manner. The surgeon begins by coupling the anastomosing and stapling attachment to the electromechanical driver and advancing the anvil portion to its fullest extent. The anvil head is then removed and inserted into the exposed proximal end. This proximal end is then stapled closed (with the coupling post protruding from the stapled proximal end). The surgeon then advances the shaft and the SBR portion of the attachment up the colon until it extends through the stapled distal end of the colon. The surgeon then couples the anvil to the advancing and retracting nut of the corresponding drive shaft. Subsequent triggering of the motor in the handle causes the anvil to retract toward the SBR portion. When the anvil portion and the SBR portion have come close enough to drive the blade and staple driver, subsequent actuation of the other trigger on the handle causes the corresponding other turning drive shaft to advance the blade and staple driver toward the flat cutting support surface of the anvil portion. The blade cuts through the stapled-closed ends of the colon, leaving the tissue which has been severed in the interior reservoir. Simultaneous with the cutting, the freshly opened ends are joined together by the series of staples which are advanced through holes in the perimeter edge of the SBR (being pressed against and closed by the opposing face of the anvil). Simultaneous with the stapling, the staple drivers push the delivery or plunger drivers forward in the dispensing chambers. The drivers push the sacs against the inward facing prongs, which breaks the sacs and releases the fibrin. The fibrin is then pushed out the channel to the cutting and stapling site. The attachment and the flexible shaft are then withdrawn from the patient.

It should be noted that inasmuch as the present invention can be used for applications and in conjunction with devices not related to an anastomosing and stapling attachment, or even colon resecting tools, but rather can be used for applications involving and in conjunction with other surgical devices, the present invention can be used alone, or with a blade, or with a stapler, or with other devices or combinations of devices to deliver medicine or other healing substances to a treatment site.

A BRIEF DESCRIPTION OF THE DRAWINGS

A DETAILED DESCRIPTION OF THE PREFERRED EMBODIMENTS

Figure 1:
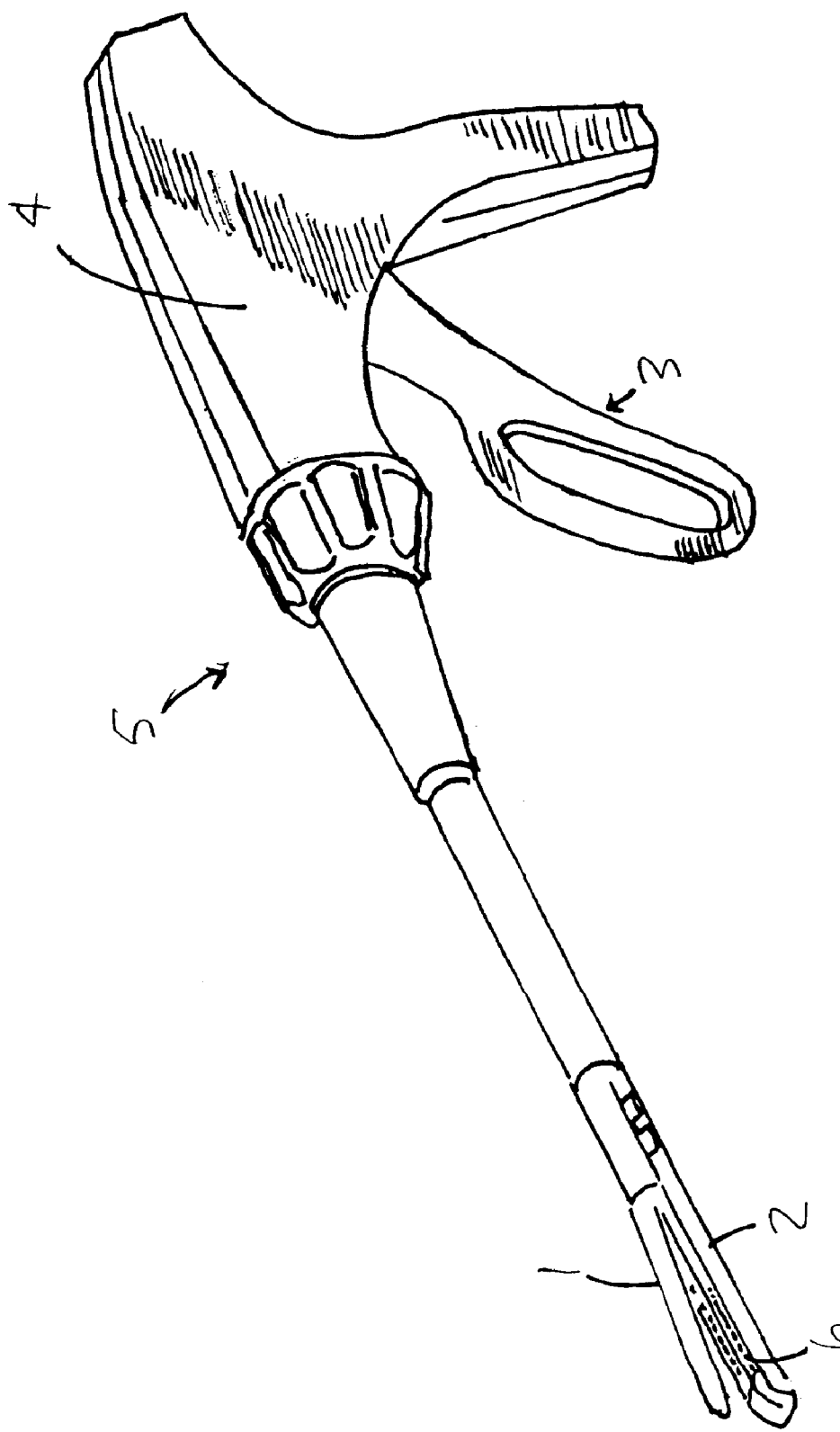
FIG. 1 is a side perspective view of a linear clamping and stapling instrument of the prior art.
Figure 2:
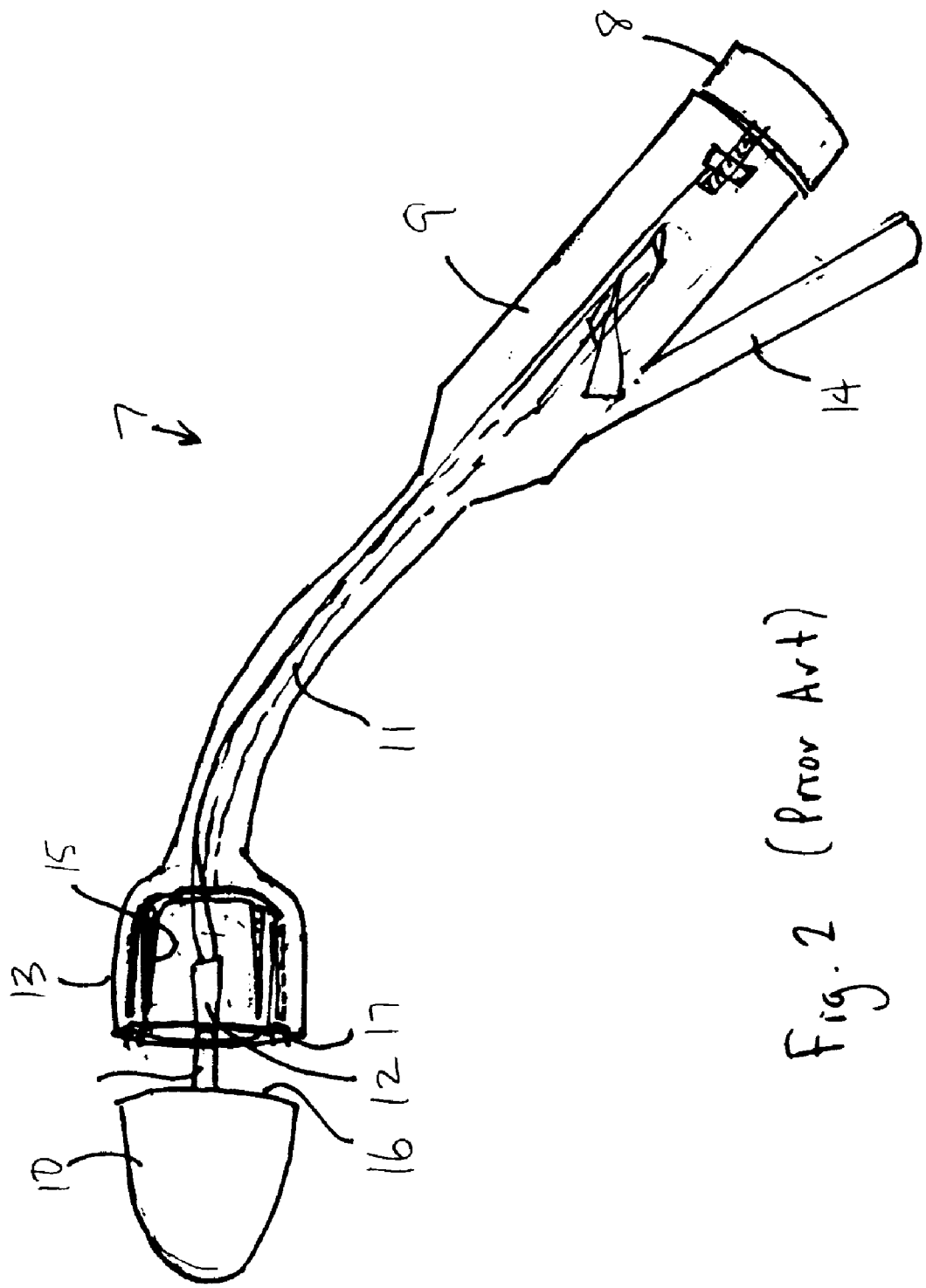
FIG. 2 is a side perspective view of an anastomosing and stapling instrument of the prior art.
Figure 3:
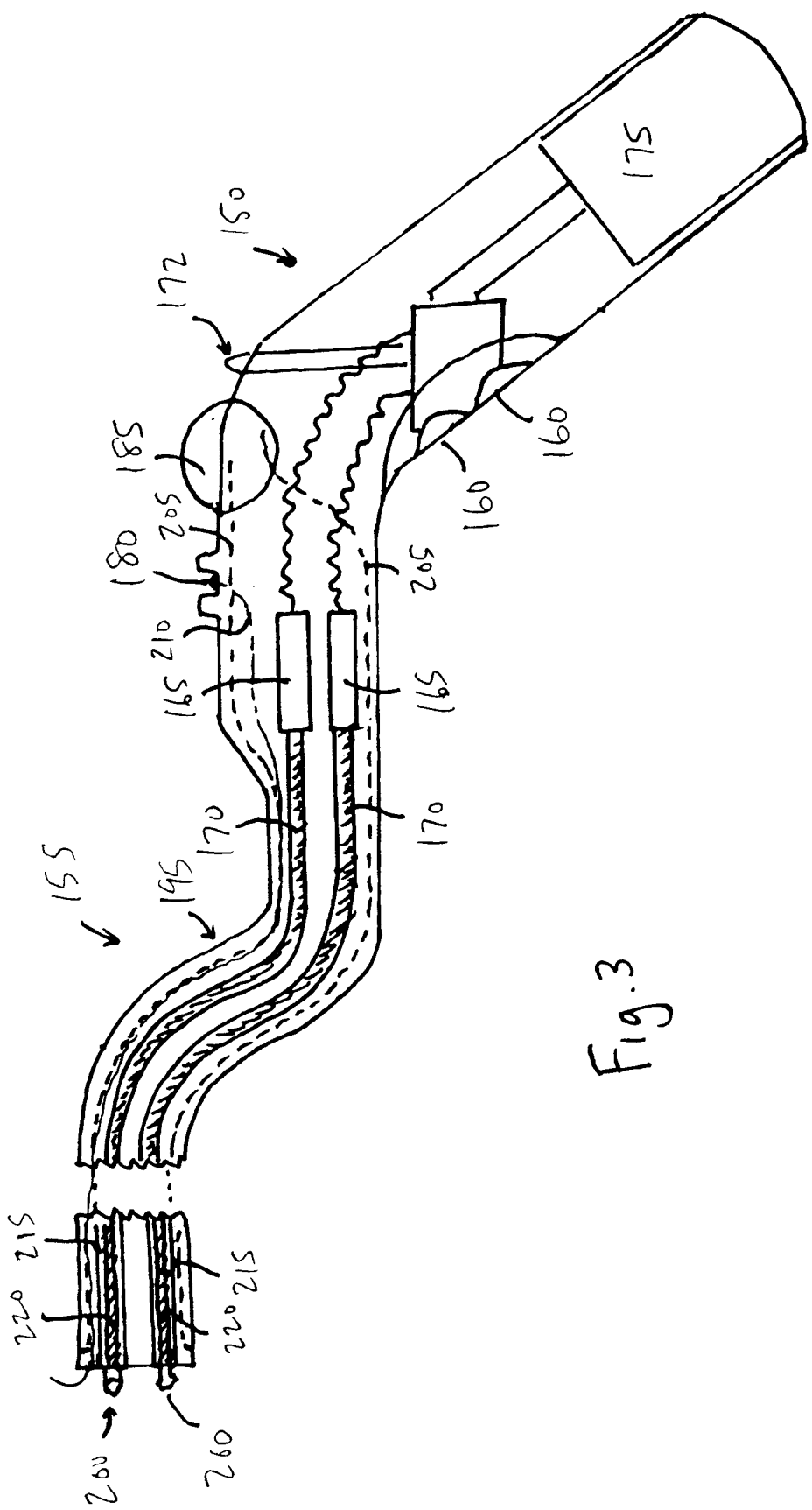
FIG. 3 is a side cutaway view of a handle and flexible shaft of an electromechanical device driver which is used to drive the anastomosing and stapling attachment described herein.
Figure 4:
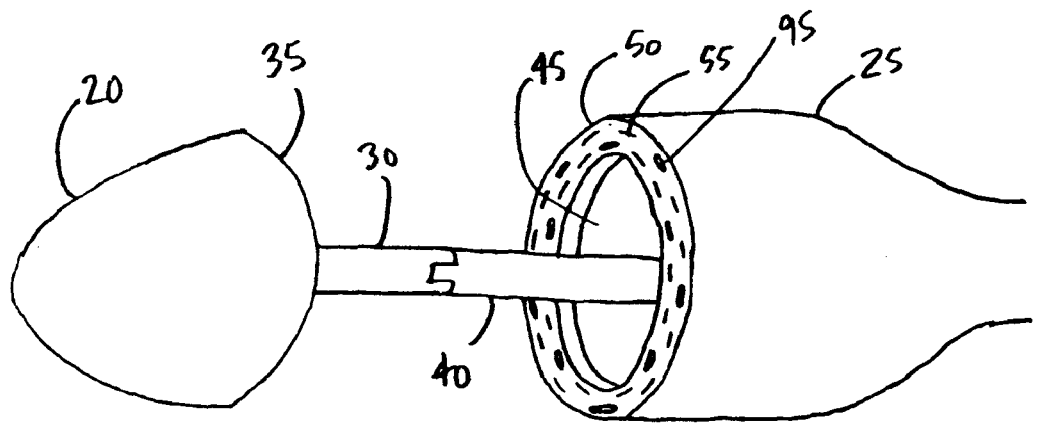
FIG. 4 is a perspective view of an anastomosing and stapling attachment having an integrated medicine delivery mechanism of the present invention.

While the present invention will be described more fully hereinafter with reference to the accompanying drawings, in which particular embodiments are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

A preferred embodiment of the medicine delivery mechanism of an anastomosing and stapling attachment according to the present invention is illustrated in FIGS. 4–9. More particularly, referring now to FIG. 4, a perspective exterior view of an anastomosing and stapling attachment in an extended position is shown. The anvil portion 20 and the staple, blade, and reservoir (SBR) portion 25 are connected by a coupling post 30 which extends from the flat cutting support surface 35 of the anvil portion 20 and is selectively coupleable and removable from the corresponding nut mounted to one of the turning drive shafts 40 of the SBR portion 25.

Figure 5:
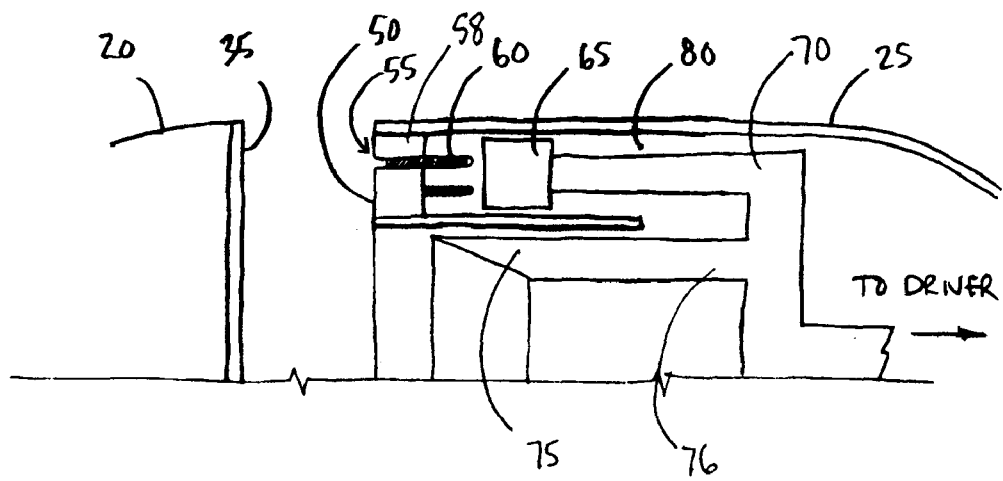
FIG. 5 is a side cutaway view of an anastomosing and stapling attachment having an integrated medicine delivery mechanism of the present invention in a preferred embodiment, showing a staple in a staple port.

Referring now also to FIG. 5, a cutaway view of the interior of the SBR portion 25 is shown. The SBR portion 25 is cylindrical in shape, and has a hollow interior, or reservoir 45. A stapling surface 50 faces axially outward toward the cutting support surface 35 of the anvil portion 20, and contains a series of staple ports 55 (formed in a staple housing 58), through which staples 60 are discharged. In addition, a series of dispensing chambers 95 are formed in lieu of staple ports 55 as shown. A series of staple drivers 65 are mounted within a staple driver shaft 80, behind corresponding staple ports 55, for driving the staples 60 therethrough. More accurately, the staple drivers 65 are a series of protuberances on the outer edge of a driving cylinder 70 which seats in the SBR portion 25 and which is connected to the second drive shaft (not shown) of the SBR portion 25. The staples 60, prior to being discharged, are mounted behind the staple ports 55 as shown and are advanced through the ports 55 by the forward motion of the staple drivers 65 and the protuberances thereof. The blade 75 is similarly cylindrical, and seats in the SBR portion adjacent the staple driver shaft 80. The blade 75 and the staple drivers 65 are mounted to the driving cylinder 70 as shown, which is connected to the second drive shaft (not shown) of the SBR portion 25.

Figure 6:
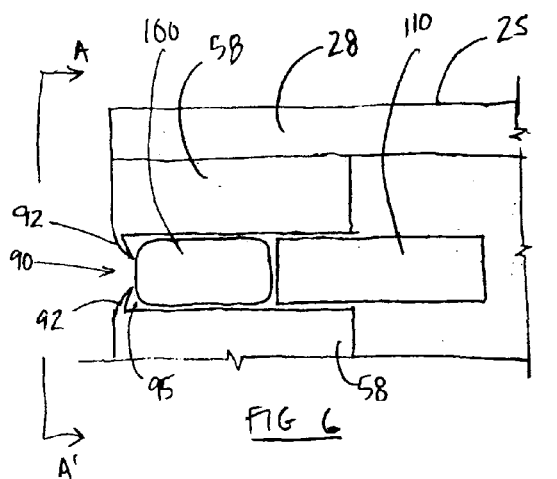
FIG. 6 is a side cutaway view of an anastomosing and stapling attachment having an integrated medicine delivery mechanism of the present invention in a preferred embodiment, showing a sac in a dispensing chamber.
Figure 7:
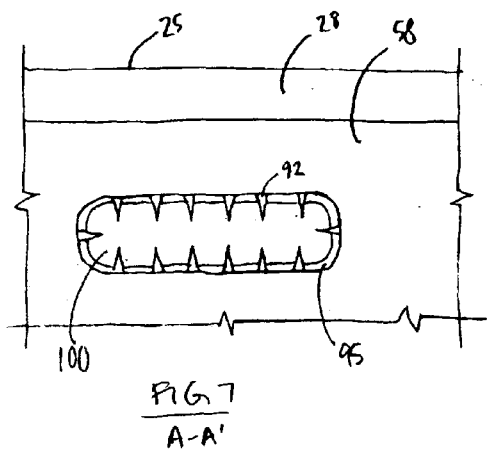
FIG. 7 is a front cutaway view of an anastomosing and stapling attachment having an integrated medicine delivery mechanism of the present invention in a preferred embodiment, showing a sac in a dispensing chamber.

Referring now to FIGS. 6 and 7, a closer cut away view of the anastamosing and stapling attachment fitted with the preferred embodiment of the present invention is shown. Illustrated is the wall 28 of the SBR portion 25 of the attachment, the staple housing 58, and a dispensing chamber 95 in lieu of a staple port 55 (FIG. 5). Similar dispensing chambers 95 are formed in lieu of staple ports 55 along the perimeter of the stapling surface 50 (best shown in FIG. 4). The dispensing chamber can be cylindrical, or have an elongated cylindrical cross-section as shown in FIG. 7, or take on other shapes. The mouth of the dispensing chamber forms a channel 90 which is lined at its innermost edge perimeter with inward facing prongs or teeth 92. The dispensing chamber 95 contains a sac 100 filled with fibrin. A delivery or plunger driver 110 travels within the dispensing chamber 95. The delivery or plunger driver 110 protrudes from the innermost end of the dispensing chamber 110 as shown, similar to the way each staple 60 protrudes from its staple port 55 in the staple housing 58, as best shown in FIG. 5.

Figure 8:
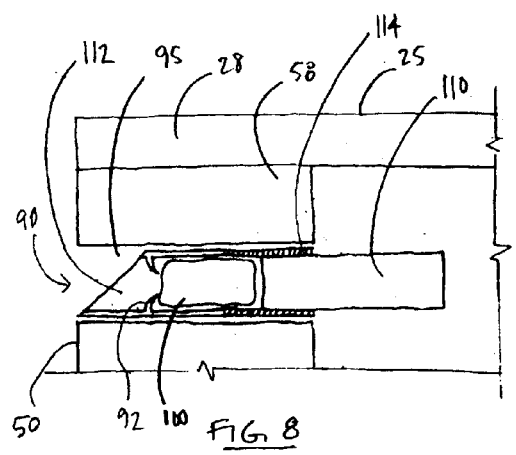
FIG. 8 is a side cutaway view of an anastomosing and stapling attachment having an integrated medicine delivery mechanism of the present invention in an alternate embodiment, showing a cannula.
Figure 9:
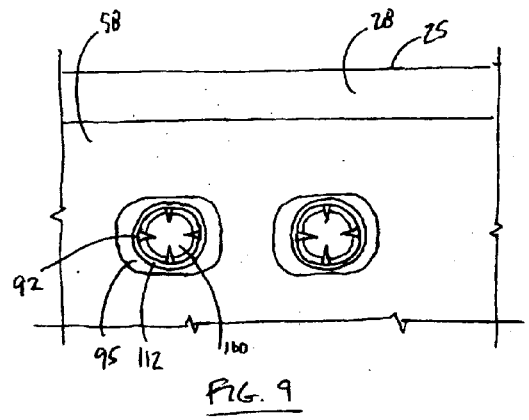
FIG. 9 is a front cutaway view of an anastomosing and stapling attachment having an integrated medicine delivery mechanism of the present invention in an alternate embodiment, showing a cannula.

Referring now to FIGS. 8 and 9, a closer cut away view of the anastamosing and stapling attachment fitted with an alternate embodiment of the present invention is shown. Many aspects of this embodiment are identical to the aspects of the preferred embodiment, and are so numbered. In this alternate embodiment, however, the channel 90 does not have inward facing prongs or teeth. Instead, the channel 90 is clear. However, in lieu of a sac of fibrin and a separate delivery or plunger driver, the dispensing chamber 95 is loaded with a cannula 112 having a sharp point. The sharp end of the cannula 112 is pointed toward the stapling surface 50 (that is, when pushed out the dispensing chamber 95, it will puncture the tissue and eventually be stopped by the flat cutting surface of the anvil (not shown)). Immediately inside the sharp end of the cannula 112, the inner perimeter of the cannula 112 is lined with inward facing prongs or teeth 92, similar to the inward facing prongs of the preferred embodiment. Inside the cannula 112 sits a sac 100 of fibrin. Behind the sac 100 is located a delivery or plunger driver 110. This delivery or plunger driver 110 is attached to the walls of the cannula 112 as shown, but is set to break away from the walls after the tip of the cannula has reached the anvil. The break away portion 114 is noted in shade.

It should be noted that the preferred embodiment and the alternate embodiment can be used in conjunction with one another, so as to deliver fibrin to both sides of the treatment site during the same procedure.

In operation (the operation of both embodiments will be described hereinbelow), the attachment is utilized once the section of the colon which is to be removed has been resected (but prior to the linear clamping and stapling step is complete). The surgeon begins by coupling the anastomosing and stapling attachment to the electromechanical driver and advancing the anvil portion 20 to its fullest extent via a triggering of the motor (not shown) in the handle (not shown). The anvil portion 20 is then decoupled from the electromechanical driver and inserted into the exposed proximal end. This proximal end is then stapled closed (with the coupling post 30 protruding from the stapled proximal end). The surgeon then advances the first turning drive shaft 40 and the SBR portion 25 of the attachment up the colon until it extends through the stapled distal end of the colon. The surgeon then re-couples the anvil portion 20, via the coupling post 30, to the first turning drive shaft 40. Subsequent reverse triggering of the motor (not shown) in the handle (not shown) causes the anvil portion 20 to retract toward the SBR portion 25, thus bringing the stapled-closed proximal and distal ends of the colon together. When the anvil portion 20 and the SBR portion 25 have come close enough to drive the blade 75 and staple driver 65, subsequent actuation of a second trigger (not shown) on the handle (not shown) causes the corresponding second turning drive shaft (not shown) to advance the blade 75 and staple driver 65 toward the flat cutting support surface 35 of the anvil portion 25. Once the blade 75 reaches the flat cutting support surface 35 of the anvil portion 25, the blade 75 cuts through the stapled-closed proximal and distal ends of the colon, leaving the now-severed tissue in the reservoir 45. Meanwhile, the staple drivers 65 (which have been advancing with the blade 75, yet positioned slightly behind the plane of the blade 75 as shown, in order to correctly time the stapling action to come immediately after the cutting action) reach the butts of the staples 60, and continue forward to push the staples 60 through the staple ports 55 and toward the stapling surface 50 and finally against the flat cutting support surface 35, which action bends the staple prongs to close the staples 60, thereby joining together the freshly cut-open proximal and distal ends of the colon.

At the same time (in the preferred embodiment) the staple drivers 65 move forward to push each delivery or plunger driver 110 through its corresponding dispensing chamber 95. As each delivery or plunger driver 110 moves forward through the dispensing chamber 95, it compresses the sac 100 of fibrin. As the sac presses against the inward facing prongs or teeth 92 of the channel 95, it tears, releasing the fibrin out through the channel 95 and onto the newly stapled tissue. Meanwhile, the blade driver 76 (FIG. 5) has moved forward, pushing the blade 75 (FIG. 5) through the newly stapled tissue and cutting away the excess. The attachment is removed, and the healing process begins, accelerated by the presence of the fibrin at the cutting and stapling site.

Alternatively, at the same time (in the alternate embodiment), the staple driver 65 (FIG. 5) moves forward to push each delivery or plunger driver 110. The delivery or plunger driver 110 first pushes the cannula 112 out the dispensing chamber 95 and through the tissue, against the flat cutting surface 35 (FIG. 5) of the anvil portion 20 (FIG. 5). Once the tip of the cannula 112 has reached the anvil 20 (FIG. 5), the delivery or plunger driver 110 continues to be pushed forward. This motion breaks the delivery or plunger driver 110 away from the walls of the cannula 112 (the break away portion 114 breaks), and thereafter the driver 110 can continue to move forward through the cannula 112 itself. As each delivery or plunger driver 110 moves forward through its cannula 112, it compresses the sac 100 of fibrin. As the sac 100 presses against the inward facing prongs 92 of the cannula 112, it tears, releasing the fibrin out through the cannula 112 and onto the opposing side of the newly stapled tissue. Meanwhile, the blade driver 76 (FIG. 5) has moved forward, pushing the blade 75 (FIG. 5) through the newly stapled tissue and cutting away the excess. The attachment is removed, and the healing process begins, accelerated by the presence of the fibrin at the cutting and stapling site.

As noted above in the Summary, an embodiment involving a compressible connection between the delivery driver and the cannula, instead of a break-away portion as described immediately above will function in a similar fashion. For example, if springs (not shown) are used in lieu of a break-away portion, once the tip of the cannula 112 has reached the anvil 20 (FIG. 5), the delivery or plunger driver 110 also continues to be pushed forward. This motion compresses the springs, and the delivery or plunger driver 110 can continue to move forward through the cannula 112 itself. As each delivery or plunger driver 110 moves forward through its cannula 112, it compresses the sac 100 of fibrin. The remainder of the operation is as described above.

While there has been described and illustrated specific embodiments of new and novel medicine delivery mechanisms, it will be apparent to those skilled in the art that variations and modifications are possible without deviating from the broad spirit and principle of the present invention which shall be limited solely by the scope of the claims appended hereto.

What is claimed is:

1. A fluid delivery device, comprising:
a dispensing chamber;
a sac arranged in the dispensing chamber and configured to contain a fluid;
a channel arranged to communicate between a treatment site and the dispensing chamber; and
a delivery driver configured to travel within the dispensing chamber with a force greater than a force needed to push the fluid through the channel;
wherein at least one of the dispensing chamber and the channel includes at least one sharpened interior portion.

2. The fluid delivery device according to claim 1, wherein the fluid includes at least one of a medicinal fluid, a substance configured to accelerate a healing process and fibrin.

3. The fluid delivery device according to claim 1, further comprising a fluid contained in the sac.

4. The fluid delivery device according to claim 3, wherein the fluid includes at least one of a medicinal fluid, a substance configured to accelerate a healing process and fibrin.

5. The fluid delivery device according to claim 1, wherein at least one the dispensing chamber and the channel includes an interior, the fluid delivery device further comprising at least one sharpened prong extending from a wall of the channel toward the interior.

6. The fluid delivery device according to claim 5, wherein the prong is directed in a direction opposite to a direction of travel of the delivery driver.

7. A fluid delivery device, comprising:
a housing including a port adapted to fit an unbent staple;
a dispensing chamber arranged in the housing and configured to contain a fluid;
a channel arranged to communicate between a treatment site and the dispensing chamber; and
a delivery driver configured to travel within the dispensing chamber with a force greater than a force needed to push the fluid through the channel.

8. The fluid delivery device according to claim 7, wherein the fluid includes at least one of a medicinal fluid, a substance configured to accelerate a healing process and fibrin.

9. The fluid delivery device according to claim 7, further comprising:
a fluid contained in the dispensing chamber;
wherein the fluid includes at least one of a medicinal fluid, a substance configured to accelerate a healing process and fibrin.

10. The fluid delivery device according to claim 7, further comprising a rotatable drive shaft arranged to drive a staple driver, the delivery driver arranged as an extension of the drive shaft.

11. The fluid delivery device according to claim 7, wherein the delivery driver is substantially cylindrical.

12. A fluid delivery device, comprising:
a dispensing chamber arranged in a housing and configured to contain a fluid;
a cannula having a sharpened distal end and arranged to travel within the dispensing chamber;
a channel arranged to communicate between a treatment site and the dispensing chamber; and
a delivery driver configured to travel within the dispensing chamber with a force greater than a force needed to push the fluid through the channel.

13. The fluid delivery device according to claim 12, wherein the fluid includes at least one of a medicinal fluid, a substance configured to accelerate a healing process and fibrin.

14. The fluid delivery device according to claim 12, further comprising a fluid contained in the dispensing chamber.

15. The fluid delivery devise according to claim 14, wherein the fluid includes at least one of a medicinal fluid, a substance configured to accelerated a healing process and fibrin.

16. The fluid delivery device according to claim 15, wherein comprising a sac arranged within the cannula and configured to enclose the fluid, the cannula including at least one sharpened interior portion.

17. The fluid delivery device according to claim 16, wherein the cannula includes an interior and at least one sharpened prong extending from a wall of the cannula toward the interior.

18. The fluid delivery device according to claim 17, wherein the prong is directed in a direction opposite a direction of travel of the delivery driver.

19. The fluid delivery device according to claim 15, further comprising a housing including a port adapted to fit an unbent staple, the dispensing chamber arranged in the housing.

20. The fluid delivery device according to claim 19, further comprising a rotatable drive shaft arranged to drive a staple driver, the delivery driver arranged as an extension of the drive shaft.

21. The fluid delivery device according to claim 19, wherein the delivery driver is substantially cylindrical.

22. The fluid delivery device according to claim 15, wherein the delivery driver is arranged as an extension of a proximal end of the cannula.

23. The fluid delivery device according to claim 22, further comprising a connector portion connecting the delivery driver and the cannula.

24. The fluid delivery device according to claim 23, wherein the connector portion is structurally weaker than at least one of the delivery driver and the cannula.

25. The fluid delivery device according to claim 23, wherein the connector portion is compressible.

26. The fluid delivery device according to claim 25, wherein the connector portion includes a spring.

27. A fluid delivery device, comprising:
a housing including an annular array of dispensing chambers, each configured to contain a fluid; and
a delivery driver arranged to travel within the dispensing chambers with a force greater than a force needed to expel the fluid from the dispensing chambers.

28. The fluid delivery device according to claim 27, further comprising a first rotatable drive shaft arranged to drive the delivery driver.

29. The fluid delivery device according to claim 27, further comprising:
an anvil portion extendable and retractable from the housing;
a plurality of staples arranged in respective staple ports arranged in the housing; and
a staple driver arranged within the housing and configured to eject and form the staples against the anvil portion.

30. The fluid delivery device according to claim 29, further comprising:
a first rotatable drive shaft configured to drive the delivery driver and the staple driver; and a second rotatable drive shaft configured to drive the anvil portion.

31. The fluid delivery device according to claim 30, wherein the first rotatable drive shaft is configured to drive the delivery driver and the staple driver independently of the second rotatable drive shaft.

32. The fluid delivery device according to claim 30, further comprising a motor arrangement configured to drive the first rotatable drive shaft and the second rotatable drive shaft.

33. The fluid delivery device according to claim 32, wherein the motor arrangement includes a first motor configured to drive the first rotatable drive shaft and a second motor configured to drive the second rotatable drive shaft.

34. The fluid delivery device according to claim 27, further comprising a sac arranged in the dispensing chamber and configured to contain the fluid.

35. The fluid delivery device according to claim 34, further comprising a fluid contained in the sac.

36. The fluid delivery device according to claim 35, wherein the fluid includes at least one of a medicinal fluid, a substance configured to accelerate a healing process and fibrin.

37. The fluid delivery device according to claim 27, further comprising a fluid contained in the dispensing chamber.

38. The fluid delivery device according to claim 37, wherein the fluid includes at least one of a medicinal fluid, a substance configured to accelerate a healing process and fibrin.

* * * * *

UNITED STATES PATENT AND TRADEMARK OFFICE
CERTIFICATE OF CORRECTION

PATENT NO. : 6,695,199 B2
DATED : February 24, 2004
INVENTOR(S) : Michael P. Whitman It is certified that error appears in the above-identified patent and that said Letters Patent is hereby corrected as shown below:

<u>Column 12,</u>
Line 13, change "wherein comprising" to -- further comprising --.

Signed and Sealed this

Fifth Day of April, 2005

JON W. DUDAS
*Director of the United States Patent and Trademark Office*